US009541435B2

(12) United States Patent
Pors et al.

(10) Patent No.: US 9,541,435 B2
(45) Date of Patent: Jan. 10, 2017

(54) NUCLEAR MAGNETIC FLOWMETER

(71) Applicant: Krohne AG, Basel (CH)

(72) Inventors: Jan Teunis Aart Pors, Oud-Beijerland (NL); Jan-Willem Ramondt, Breda (NL)

(73) Assignee: Krohne AG, Basel (CH)

( * ) Notice: Subject to any disclaimer, the term of this patent is extended or adjusted under 35 U.S.C. 154(b) by 503 days.

(21) Appl. No.: 14/208,371

(22) Filed: Mar. 13, 2014

(65) Prior Publication Data

US 2014/0266188 A1   Sep. 18, 2014

(30) Foreign Application Priority Data

Mar. 13, 2013   (DE) .................. 10 2013 004 267

(51) Int. Cl.
| | | |
|---|---|---|
| *G01F 1/716* | (2006.01) | |
| *G01R 33/563* | (2006.01) | |
| *G01R 33/30* | (2006.01) | |
| *G01N 24/08* | (2006.01) | |

(52) U.S. Cl.
CPC ......... *G01F 1/716* (2013.01); *G01R 33/56308* (2013.01); *G01N 24/08* (2013.01); *G01R 33/307* (2013.01)

(58) Field of Classification Search
CPC . G01F 1/716; G01R 33/56308; G01R 33/307; G01N 24/08
See application file for complete search history.

(56) References Cited

U.S. PATENT DOCUMENTS

| | | |
|---|---|---|
| 3,471,774 A | 10/1969 | Muschinske et al. |
| 3,564,400 A | 2/1971 | Pike et al. |
| 4,722,231 A | 2/1988 | Tanaka et al. |
| 4,782,295 A | 11/1988 | Lew |
| 4,785,245 A | 11/1988 | Lew et al. |
| 4,901,018 A | 2/1990 | Lew |
| 6,111,408 A | 8/2000 | Blades et al. |
| 6,269,530 B1 | 8/2001 | Armitage et al. |
| 6,452,390 B1 | 9/2002 | Wollin |
| 2013/0009645 A1 | 1/2013 | Miki |
| 2013/0018602 A1 | 1/2013 | Ong et al. |

FOREIGN PATENT DOCUMENTS

DE   102009002053 A1   10/2010

*Primary Examiner* — Rodney Bonnette
(74) *Attorney, Agent, or Firm* — David S. Safran

(57) ABSTRACT

A nuclear magnetic flowmeter is disclosed. The nuclear magnetic flowmeter includes a magnetization device located around a straight measuring tube for producing a magnetic field in a medium. The flowmeter also includes a gradient coil that produces a gradient in the field. The flowmeter further includes a signal coil that excites the medium and that detects the result of the excitation. Additionally, the flowmeter includes a coil insulating frame and a sealed housing. The housing is along a longitudinal axis of the tube and has a first face side and a second face side having openings through which the tube is routed. The magnetization device is provided in the interior of the housing. The gradient coil and the signal coil are located in a space between the tube and magnetization device that is penetrated by the field. The gradient coil and/or the signal coil are located on the frame.

17 Claims, 3 Drawing Sheets

NUCLEAR MAGNETIC FLOWMETER

BACKGROUND OF THE INVENTION

Field of the Invention

The present invention relates to a nuclear magnetic flowmeter. More specifically, the present invention relates to a nuclear magnetic flowmeter with a straight measuring tube through which a multiphase medium can flow. In embodiments, the nuclear magnetic flowmeter includes a magnetization device that is located around the measuring tube for producing a magnetic field in the medium flowing though the measuring tube. The nuclear magnetic flowmeter also includes at least one gradient coil for producing a gradient in the magnetic field and/or at least one signal coil that excites the medium, and/or detects a result of the excitation. Additionally, the nuclear magnetic flowmeter includes a first coil insulating frame and a housing. The housing has a first face side and a second face side along a longitudinal axis of the measuring tube. In the first face side, there is a first housing opening, and in the second face side there is a second housing opening through which the measuring tube is routed. The magnetization device is provided in the interior of the housing. The housing, aside from the two housing openings, is tightly sealed. The gradient coil and the signal coil are located in a space between the measuring tube and magnetization device, wherein the space is penetrated by the magnetic field. The at least one gradient coil and/or the signal coil or at least one signal coil are located on the first coil insulating frame.

Description of Related Art

The atomic nuclei of the elements which have a nuclear spin also have a magnetic moment which is caused by the nuclear spin. The nuclear spin can be construed as angular momentum which can be described by a vector. Accordingly, the magnetic moment can also be described by a vector which is aligned parallel to the vector of the angular momentum. The vector of the magnetic moment of an atomic nucleus in the presence of a macroscopic magnetic field is aligned parallel to the vector of the macroscopic magnetic field at the location of the atomic nucleus. The vector of the magnetic moment of the atomic nucleus precesses around the vector of the macroscopic magnetic field at the location of the atomic nucleus. The frequency of the precession is called the Larmor frequency $\omega_L$ and is proportional to the value of the magnetic field strength B. The Larmor frequency is computed according to $\omega_L = \gamma B$, in which $\gamma$ is the gyromagnetic ratio which is maximum for hydrogen nuclei. The precession of the magnetic moment of an atomic nucleus is an alternating magnetic field with the Larmor frequency which can induce an electrical signal with the same frequency into a coil.

Nuclear magnetic resonance measurement methods are measurement methods that influence the precession of atomic nuclei of a medium in the presence of a macroscopic magnetic field through excitation by means of a controlled magnetic field and that evaluate a result of the excitation. The prerequisite for the measurement of a multiphase medium is that the individual phases of the medium can be excited to distinguishable nuclear magnetic resonances.

Nuclear magnetic flowmeters are measurement devices that implement nuclear magnetic resonance methods. They can measure flow velocities of the individual phases of the medium in a measuring tube and relative proportions of the individual phases in the multiphase medium. Nuclear magnetic flowmeters can be used, for example, for measuring the flow rate of a multiphase medium which has been conveyed from oil sources. This medium consists essentially of the liquid phases of crude oil and salt water, and the gaseous phase natural gas. All these phases contain hydrogen nuclei, which are necessary for nuclear magnetic resonances and are excitable to different nuclear magnetic resonances.

The measurement of the multiphase medium which has been conveyed from oil sources can also take place with test separators. The conveyed medium is introduced into a test separator over a time interval, wherein the test separator separates the individual phases of the medium from one another and determines the proportions of the individual phases in the medium. However test separators, in contrast to nuclear magnetic flowmeters, cannot reliably measure proportions of crude oil smaller than 5%. Since the proportion of crude oil of any oil source continuously decreases, and because the proportion of crude oil of a host of oil sources can already be less than 5%, it is not currently possible to economically exploit these oil sources using test separators. Further, in order to exploit such sources having very small proportions of oil, flowmeters that are accurate for mediums consisting of several phases are necessary. In particular nuclear magnetic flowmeters are suitable for this purpose.

In nuclear magnetic flowmeters, a magnetization device and a gradient coil produce a magnetic field along which the magnetic moments of the atomic nuclei of the multiphase medium are first aligned. The magnetic field produced by the magnetization device is homogeneous in the medium that is flowing through the measuring tube. The magnetic field is usually produced by permanent magnets that are located in the magnetization device, such as a Halbach array. Different measurement methods dictate a gradient in the magnetic field that penetrates the medium. This gradient is produced by superposition of the homogenous magnetic field with an inhomogeneous field produced by the gradient coil.

A controlled magnetic field that excites the precessing atomic nuclei can be produced by at least one signal coil. This signal coil, or other signal coils, can also be used as a sensor for an alternating magnetic field produced by the precessing atomic nuclei. Conventionally, the coils, (i.e. the gradient coils) and the signal coils are located in a space between the magnetization device and the measuring tube that is penetrated by the magnetic field.

In the interior of the nuclear magnetic flowmeter, a housing accommodates the magnetization device and tightly seals the interior relative to the exterior environment. The meaning of "tightly" depends on the purpose of the nuclear magnetic flowmeter. In embodiments, tightness can be specified for touching and foreign bodies. In other embodiments, tightness depends on moisture and water on the other according to "Degrees of protection provided by enclosures" (Standard EN 60529, published Jan. 1, 1992). Tightness for touching and foreign bodies is defined via the size of the foreign bodies and in the International Protection Code extends to dust-tightness (Ingress Protection Rating IP 6x). Tightness with respect to moisture and water can be given for example for temporary immersion (Ingress Protection Rating IPx7). The tightness can also be specified with respect to explosion protection, specifically by the type of explosion protection. Thus, the tightness can be specified by a pressure-tight encapsulation according to "Explosive atmospheres. Equipment protection by flameproof enclosures 'd'" (Standard EN 60079-1, published Aug. 31, 2007) or by increased safety according to "Explosive atmospheres. Equipment protection by increased safety 'e'" (Standard EN 60079-7, published Jan. 31, 2007).

Nuclear magnetic flowmeters conventionally have housings whose manufacture is complex due to the demands for tightness. In particular, the construction and production of the housing in the region between the measuring tube and the magnetization device is complex and expensive.

SUMMARY OF THE INVENTION

The object of this present invention is to provide a nuclear magnetic flowmeter with an improved and simplified structure.

The nuclear magnetic flowmeter in accordance with aspects of the present invention includes a first coil suspension between the first coil insulating frame and a first face side of a housing. Further, in accordance with aspects of the present invention, the nuclear magnetic flowmeter includes a second coil suspension between the first coil insulating frame and a second face side of the housing. A top of the first coil insulating frame, at least in a first section between the first coil suspension and the second coil suspension, is a closed surface. The first coil suspension seals the first coil insulating frame with the first face side. The second coil suspension seals the first coil insulating frame with the second face side. The housing, together with the first coil insulating frame and the coil suspensions, is tightly sealed.

The nuclear magnetic flowmeter in accordance with aspects of the present invention advantageously reduces the number of components. As a result, the manufacture of the nuclear magnetic flowmeter is simplified. More specifically, the additional layout of the first coil insulating frame as part of the housing eliminates a separate housing element of conventional flowmeters that seals the interior of the housing in a first section relative to the exterior. The elimination of this housing element enables nuclear magnetic flowmeters in accordance with aspects of the present invention to be more compact than conventional flowmeters in the radial direction relative to a longitudinal axis of the measuring tube.

Embodiments of the nuclear magnetic flowmeter in accordance with aspects of the present invention include a first coil insulating frame that is tubular at least in a first section. The tubular section of the first coil insulating frame can be inserted into the two coil suspensions along the longitudinal axis of the measuring tube. As used herein, "tubular" refers to any closed outer cross sectional contour of the first coil insulating frame with reference to the longitudinal axis. Accordingly, not only a round outer cross section of the first coil insulating frame is provided. Additionally, the insertion capacity of the first coil insulating frame is ensured in the first section because the cross sectional area of the tubular section of the first coil insulating frame is matched to the free cross sectional area between the measuring tube and the magnetization device. Due to the insertion capacity of the first coil insulating frame, which also simultaneously seals the housing, the assembly of the nuclear magnetic flowmeter in accordance with aspects of the present invention is simplified.

Additionally, embodiments of the nuclear magnetic flowmeter in accordance with aspects of the present invention include a first coil insulating frame having a flange with one flange side that borders the first face side of the housing. There is also a seal between the first face side and the flange side. Moreover, on the second face side of the housing around the second housing opening, there is a carrier ring having a first ring side and a second ring side. The first ring side borders the second face side of the housing and the second ring side borders the top of the first coil insulating frame. Between the first ring side of the carrier ring and the second face side of the housing there is a seal. And, between the second ring side of the carrier ring and the top of the first coil insulating frame there is also a seal. These seals ensure tightness according to the demands which are imposed on the housing.

In embodiments, recesses for accommodating the seals are provided in the first ring side and in the second ring side of the carrier ring, and in the flange side of the flange. The contour of the recesses can be circular. In embodiments, the seal is an elastic material contoured according to the recesses formed in carrier ring and pressed together at contact sites.

The flange of the coil body can be provided with holes for routing screws through, and threads for accommodating the screws can be made in the housing on the first face side. The two coil suspensions, together with the screw connection, ensure fixing of the first coil insulating frame on the housing.

It is also advantageous to make the first coil insulating frame for throughflow of the medium such that the measuring tube is also eliminated. This provides a nuclear magnetic flowmeters that is more compact in the radial extension relative to the longitudinal axis of the measuring tube. The execution of the first coil insulating frame for throughflow with the medium entails essentially sufficient pressure tightness relative to the pressure of the medium, relative chemical resistance to the components of the medium and of course also low wear by the flow of the medium.

In embodiments, when at least in a first section of the first coil insulating frame is made tubular, an adapter is provided between the seal which has been inserted into the recess in the second ring side of the carrier ring and the top of the tubular section of the first coil insulating frame on the top of the tubular section of the first coil insulating frame. The adapter, together with the seal, enables movement of the first coil insulating frame along the longitudinal axis of the measuring tube without adversely affecting the tightness. If the first coil insulating frame is screwed to the housing on the flange, the adapter and the seals allow longitudinal movement of the first coil insulating frame, as is formed for example by different thermal expansions of the first coil insulating frame and of the housing. In this way, mechanical stresses in the housing and in the first coil insulating frame can be avoided.

In accordance with aspects of the present invention, at least the gradient coil or at least one of the gradient coils and/or the signal coil and/or at least one of the signal coils is/are located on a second coil insulating frame. This second coil insulating frame can be located on the first coil insulating frame. The arrangement can be either between the measuring tube and the first coil insulating frame or between the first coil insulating frame and the magnetization device.

When the first coil insulating frame is made tubular in the first section, it can be advantageous to make the second coil insulating frame tubular in a second section, such that especially the tubular section of the second coil insulating frame can be pushed into the tubular section of the first coil insulating frame along the longitudinal axis of the measuring tube. Preferably the second coil insulating frame also has a flange. This flange can be provided with holes for routing screws through, and in the housing on the first face side threads can be made for accommodating the screws.

If both the first coil insulating frame is provided with a flange and the flange is provided with holes for routing screws through and also the second coil insulating frame is provided with a flange and the flange is provided with holes for routing screws through, it is recommended that the holes on the first coil insulating frame and the second coil insulating frame are arranged flush so that the two coil insulating frames can be attached to the housing with the same screws. This further simplifies the assembly of the nuclear magnetic flowmeter in accordance with aspects of the present invention.

It can also be advantageous to arrange either the gradient coils on the first coil insulating frame and the signal coils on the second coil insulating frame or to arrange the signal coils on the first coil insulating frame and the gradient coils on the second coil insulating frame. In this way, the modules for producing the gradient in the magnetic field and for excitation and for detection of the action of the excitation are separated from one another and, thus, can also be replaced separately and can be adapted to different purposes. Of course, all gradient coils and signal coils can also be located on the first coil insulating frame.

Since both the first coil insulating frame and also the second coil insulating frame are located at least in part in the magnetic field, at least these parts of the frames need to consist of a material which does not adversely affect the magnetic field. Accordingly, suitable materials for the two coil insulating frames include fiber composites, and especially glass fiber-reinforced composites. Of course, the two coil insulating frames can also be produced from other materials in the regions which do not lie in the magnetic field.

In particular there are various possibilities for embodying and developing the nuclear magnetic flowmeter in accordance with aspects of the present invention. For these purposes, reference is made to the exemplary embodiments described below in conjunction with the drawings.

DETAILED DESCRIPTION OF THE INVENTION

Figure 1:
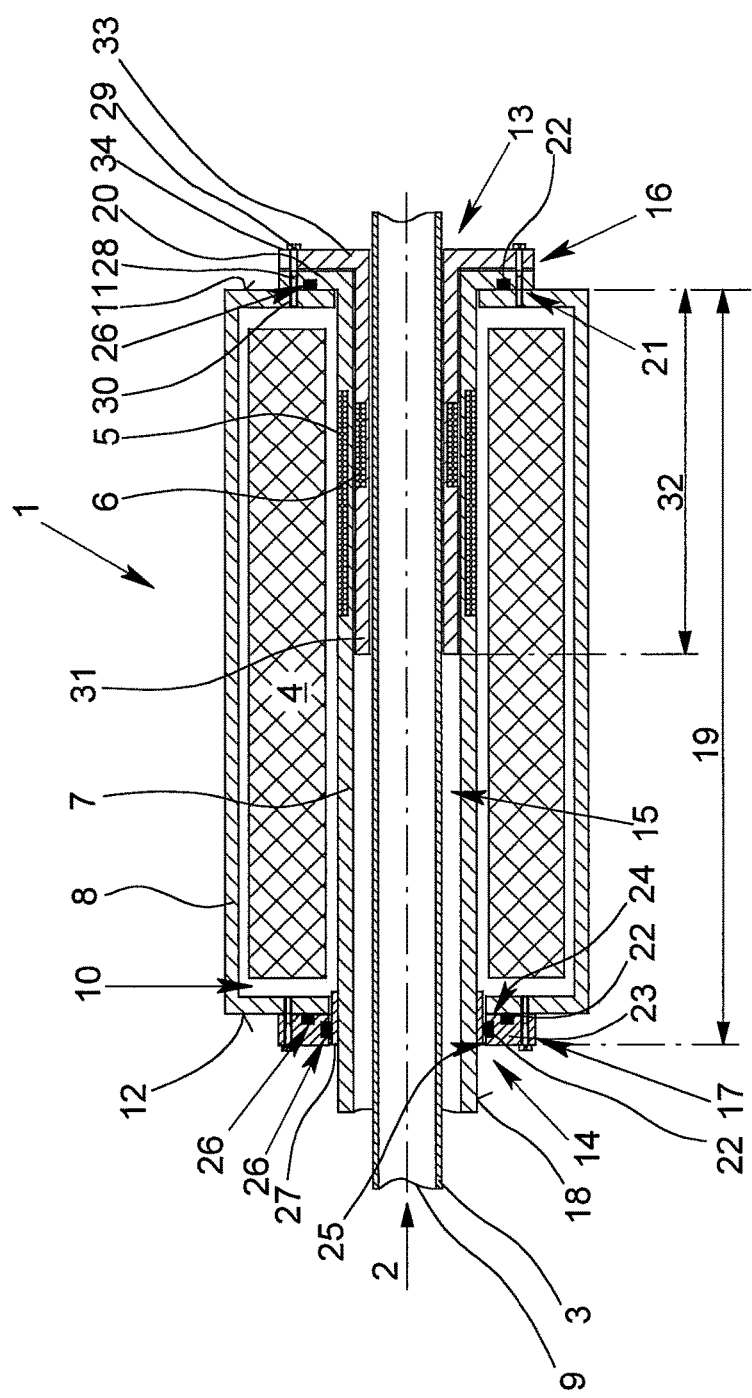
FIG. 1 shows a first exemplary embodiment of a nuclear magnetic flowmeter with a measuring tube and a first and a second coil insulating frame in accordance with aspects of the present invention.

FIG. 1 shows important elements of a first exemplary embodiment of the nuclear magnetic flowmeter 1 in accordance with aspects of the present invention. A multiphase medium 2 flows through a straight measurement tube 3. Around the measuring tube 3 is a magnetization device 4 that produces a homogeneous magnetic field in the medium 2 flowing through the measuring tube 3. A gradient coil 5 generates an inhomogeneous magnetic field in the medium 2 flowing through the measuring tube 3. Superposition of the two magnetic fields results in a magnetic field with a gradient in the medium 2. A signal coil 6 is used both for excitation of the medium 2 and also for detecting the result of the excitation. The gradient coil 5 is located on a first coil insulating frame 7. The nuclear magnetic flowmeter 1 also comprises a housing 8, the housing 8 having a first face side 11 and a second face side 12 along the longitudinal axis 9 of the measuring tube 3. In the first face side 11 there is a first housing opening 13 and in the second face side 12 there is a second housing opening 14 for routing the measuring tube 3 through. The magnetization device is provided in the interior 10 of the housing 8. The housing 8, aside from the two housing openings 13, 14, is tightly sealed in accordance with Ingress Protection Rating IP 67. Accordingly, it is dustproof and tight when temporarily immersed. Both the gradient coil 5 and also the signal coil 6 are located in the space 15 between the measuring tube 3 and the magnetization device 4, which space is penetrated by the magnetic field.

Between the first coil insulating frame 7 and the first face side 11, a first coil suspension 16 is made, and between the first coil insulating frame 7 and the second face side 12 a second coil suspension 17 is made. The top 18 of the first coil insulating frame 7 in a first section 19 between the first coil suspension 16 and the second coil suspension 17 is a closed surface, and the first coil insulating frame 7 in the first section is tubular with a round cross sectional contour.

A flange 20 is molded onto the tubular section of the first coil insulating frame 7. The flange 20 with one flange side 21 borders the first face side 11 of the housing 8. There is a sealing element 22 between the first face side 11 and the flange side 21 of the flange 20. On the second face side 12 of the housing 8 around the second housing opening 14 there is a carrier ring 23 with a first ring side 24 and a second ring side 25. The first ring side 24 borders the second face side 12 of the housing 8, and the second ring side 25 borders the top 18 of the tubular section of the first coil insulating frame 7. Both between the first ring side 24 of the carrier ring 23 and the second face side 12 of the housing 8, as well as between the second ring side 25 of the carrier ring 23 and the top 18 of the tubular section of the first coil insulating frame 7, there is one sealing element 22 at a time. There are concentric recesses 26 for elastic ring-shaped seals, such as sealing element 22 in the first ring side 24, and the second ring side 25 of the carrier ring 23 and in the flange side 21 of the flange 20.

The first coil insulating frame 7 consists essentially of a tubular section and a flange 20 which has been molded onto it. The cross sectional area with reference to the longitudinal axis 9 of the tubular section of the first coil insulating frame 7 is matched to the free space in the radial direction with reference to the longitudinal axis 9 of the measuring tube 3 between the measuring tube 3 and the magnetization device 4. As such, the tubular section of the first coil insulating frame 7 can be inserted into the two coil suspensions 16, 17 along the longitudinal axis 9.

There is an adapter 27 between the sealing element 22 which has been inserted into the recess 26 in the second ring side 25 of the carrier ring 23 and the top 18 of the tubular section of the first coil insulating frame 7 on the top 18 of the tubular section of the first coil insulating frame 7. This adapter 27 is a metal ring which is in contact with the sealing element 22 and which tightly seals it. The adapter 27 together with the sealing element 22 ensures a movement of the first coil insulating frame 7 along the longitudinal axis 9 of the measuring tube without adversely affecting the tightness of the housing 8.

In the flange 20 parallel to the longitudinal axis 9 of the measuring tube 3 there are holes 28 for routing screws 29 through on a circle arranged concentrically around the longitudinal axis 9 and they are uniformly distributed on this circle. Threads 30 flush with the holes 28 are made for the screws 29 on the first face side 11 in the housing 8.

The first coil suspension 16 encompasses the flange 20 of the coil insulating frame 7, wherein flange is provided with the recess 26 and the holes 28, the sealing element 22 for this recess 26, the threads 30 in the first face side 11 of the housing 8, and the screws 29. The second coil suspension 17 encompasses the carrier ring 23, the recess 26, which is provided with a sealing element 22 in the first ring side 24, the recess 26, which is provided with a sealing element 22 in the second ring side 25, and the adapter 27. Consequently the first coil suspension 16 seals the first coil insulating frame 7 with the first face side 11 and the second coil suspension 17 seals the first coil insulating frame 7 with the second face side 12. The interior 14 of the housing 8 is thus sealed tight relative to the exterior according to Ingress Protection Rating IP 67.

The signal coil 6 is located on the second coil insulating frame 31. The second coil insulating frame 31 is made tubular in a second section 32, such that the tubular section of the second coil insulating frame 31 can be inserted into the space between the tubular section of the first coil insulating frame 7 and the measuring tube 3 along the longitudinal axis 9. A flange 33 is molded onto the tubular section of the second coil insulating frame 31. The flange 33 of the second coil insulating frame 31 is provided with holes 34 which are flush with the holes 28 in the flange 20. Thus, it is possible to fix the first coil insulating frame 7 and the second coil insulating frame 31 with the same screws 29 on the first face side 11 of the housing 8.

Figure 2:
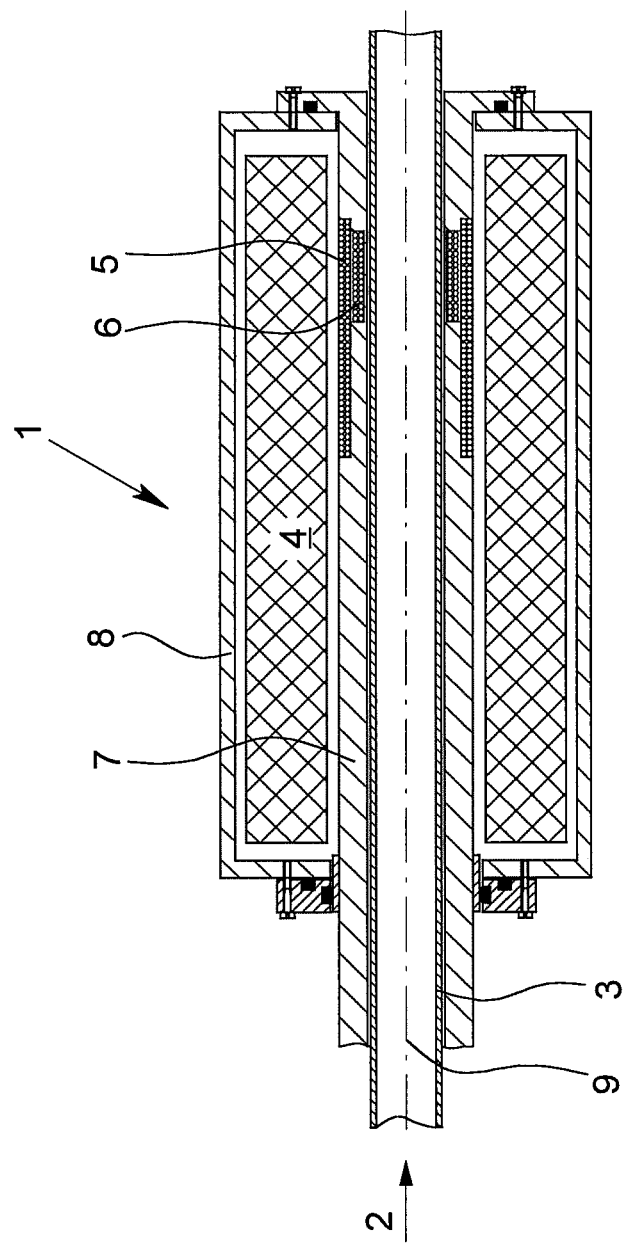
FIG. 2 shows a second exemplary embodiment of a nuclear magnetic flowmeter with a measuring tube and a first coil insulating frame in accordance with aspects of the present invention.

FIG. 2 shows a second exemplary embodiment of the nuclear magnetic flowmeter 1 in accordance with aspects of the present invention. Only the differences from the first exemplary embodiment which is shown in FIG. 1 are detailed below. In the exemplary embodiment shown in FIG. 2, in addition to the gradient coil 5, there is also the signal coil 6 on the first coil insulating frame 7. As such, a second coil insulating frame is not necessary.

In this way the number of components of the nuclear magnetic flowmeter 1 can be further reduced. Thus, the structure can be further simplified.

Figure 3:
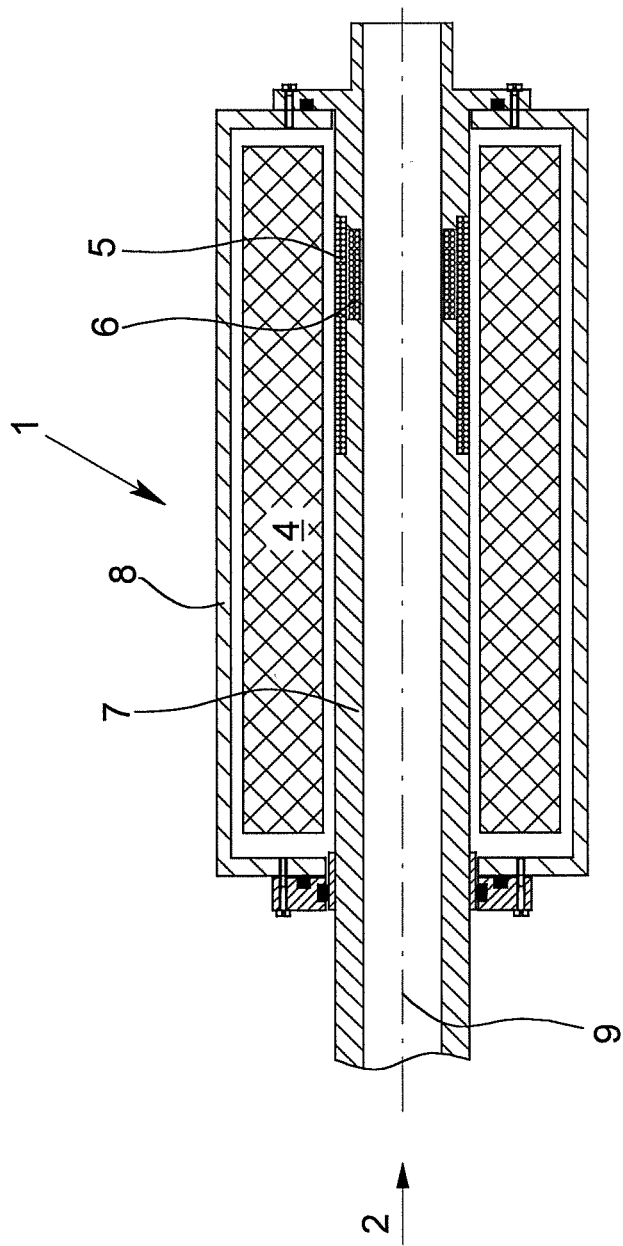
FIG. 3 shows a third exemplary embodiment of a nuclear magnetic flowmeter with a first coil insulating frame in accordance with aspects of the present invention.

FIG. 3 shows a third exemplary embodiment of the nuclear magnetic flowmeter 1 in accordance with aspects of the present invention. Here only the differences from the first exemplary embodiment which is shown in FIG. 1 are also detailed below. In the exemplary embodiment shown in FIG. 3, as already in the exemplary embodiment shown in FIG. 2, both the gradient coil 5 and also the signal coil 6 are located on the first coil insulating frame 7. Moreover the first coil insulating frame 7 is also made for throughflow with the medium 2. As such, in addition to the second coil insulating frame 31, the measuring tube 3 is also eliminated.

What is claimed is:

1. A nuclear magnetic flowmeter, comprising:
   a straight measuring tube through which a multiphase medium can flow;
   a magnetization device around the measuring tube that provides a magnetic field in the medium;
   at least one gradient coil that produces a gradient in the magnetic field and/or at least one signal coil, for exciting the medium and/or detecting the result of the excitation; and
   a first coil insulating frame and a housing,
   wherein:
      the housing has a first face side and a second face side along a longitudinal axis of the measuring tube;
      the first face side includes a first housing opening and the second face side includes a second housing opening for routing the measuring tube through;
      the magnetization device is provided in the interior of the housing;
      the housing is tightly sealed aside from the two housing openings;
      the at least one gradient coil and/or the at least one signal coil are located in a space penetrated by the magnetic field between the measuring tube and the magnetization device;
      the at least one gradient coil and/or the at least one signal coil are located on the first coil insulating frame;
      a first coil suspension is between the first coil insulating frame and the first face side of the housing;
      a second coil suspension is between the first coil insulating frame and the second face side of the housing;
      a top of the first coil insulating frame, at least in a first section between the first coil suspension and the second coil suspension, is a closed surface;
      the first coil suspension seals the first coil insulating frame with the first face side of the housing;
      the second coil suspension seals the first coil insulating frame with the second face side of the housing; and
      the housing together with the first coil insulating frame and the coil suspensions is tightly sealed.

2. The nuclear magnetic flowmeter according to claim 1, wherein:
   the first coil insulating frame that is tubular in the first section; and
   the first tubular section of the first coil insulating frame can be inserted into the two coil suspensions along the longitudinal axis.

3. The nuclear magnetic flowmeter according to claim 1, wherein:
   the first coil insulating frame has a flange with one flange side that borders the first face side of the housing;
   a seal is between the first face side of the housing and the flange side of the flange;
   the second face side of the housing around the second housing opening has a carrier ring with a first ring side and a second ring side;
   the first ring side of the carrier ring borders the second face side of the housing;
   the second ring side of the carrier ring borders the top of the first coil insulating frame;
   between the first ring side of the carrier ring and the second face side of the housing there is a seal; and
   between the second ring side of the carrier ring and the top of the first coil insulating frame there is a seal.

4. The nuclear magnetic flowmeter according to claim 3, wherein in the two ring sides of the carrier ring and in the flange side of the flange there are recesses for accommodating the seal.

5. The nuclear magnetic flowmeter according to claim 3 further comprising:
   an adapter between the seal inserted into a recess in the second ring side of the carrier ring and the top of the first tubular section of the first coil insulating frame on the top of the first tubular section of the first coil insulating frame,
   wherein the adapter, together with the seal, enables a movement of the first coil insulating frame along the longitudinal axis of the measuring tube without adversely affecting the tightness.

6. The nuclear magnetic flowmeter according to claim 3, wherein the flange is provided with holes for routing screws through and threads for accommodating the screws are made in the housing on the first face side.

7. The nuclear magnetic flowmeter according to claim 6, wherein the holes in the flange of the first coil insulating frame and in the flange of a second coil insulating frame are flush.

8. The nuclear magnetic flowmeter according to claim 1, wherein the gradient coil or at least one gradient coil and/or the at least one signal coil or one of the signal coils are located on a second coil insulating frame.

9. The nuclear magnetic flowmeter according to claim 8, wherein the second coil insulating frame is located on the first coil insulating frame.

10. The nuclear magnetic flowmeter according to claim 8, wherein:
the second coil insulating frame is tubular in a second section; and
the second tubular section of the second coil insulating frame can be inserted into the first tubular section of the first coil insulating frame along the longitudinal axis.

11. The nuclear magnetic flowmeter according to claim 8, wherein the second coil insulating frame has a flange.

12. The nuclear magnetic flowmeter according to claim 11, wherein:
the flange of the second coil insulating frame is provided with holes for routing screw through; and
threads for accommodating the screws are made in the housing on the first face side.

13. The nuclear magnetic flowmeter according to claim 12, wherein the holes in the flange of the first coil insulating frame and in the flange of the second coil insulating frame are flush.

14. The nuclear magnetic flowmeter according to claim 1, wherein the first coil insulating frame is made for through-flow with the medium.

15. The nuclear magnetic flowmeter according to claim 1, wherein only the at least one gradient coil is located on the first coil insulating frame.

16. The nuclear magnetic flowmeter according to claim 1, wherein the first coil insulating frame and/or a second coil insulating frame consist essentially of a fiber composite.

17. The nuclear magnetic flowmeter according to claim 16, wherein the fiber composite is a glass fiber-reinforced composite.

* * * * *